United States Patent
Liu et al.

(10) Patent No.: US 11,319,569 B2
(45) Date of Patent: May 3, 2022

(54) PREPARATION METHOD AND APPLICATION THEREOF OF PEPTIDES WITH ANTI-LIPID-OXIDATION CAPABILITY

(71) Applicant: Jiangnan University, Wuxi (CN)

(72) Inventors: Yuanfa Liu, Wuxi (CN); Zhaojun Zheng, Wuxi (CN); Jiaxin Li, Wuxi (CN); Yongjiang Xu, Wuxi (CN); Yin Chen, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 17/136,308

(22) Filed: Dec. 29, 2020

(65) Prior Publication Data

US 2021/0115488 A1 Apr. 22, 2021

Related U.S. Application Data

(63) Continuation of application No. PCT/CN2019/113571, filed on Oct. 28, 2019.

(30) Foreign Application Priority Data

Feb. 28, 2019 (CN) .......................... 201910150621.0

(51) Int. Cl.
  *C12P 21/06* (2006.01)
  *C07K 1/30* (2006.01)
  *C12N 9/50* (2006.01)

(52) U.S. Cl.
  CPC ................ *C12P 21/06* (2013.01); *C07K 1/30* (2013.01); *C12N 9/50* (2013.01)

(58) Field of Classification Search
  CPC .............. C12P 21/06; C07K 1/30; C12N 9/50
  USPC ......................................................... 435/272
  See application file for complete search history.

(56) References Cited

FOREIGN PATENT DOCUMENTS

| CN | 102796795 A | 11/2012 |
| CN | 105039476 A | 11/2015 |
| CN | 108220374 A | 6/2018 |
| CN | 109097424 A | 12/2018 |
| CN | 109797183 A | 5/2019 |
| WO | 2012075570 A1 | 6/2012 |

OTHER PUBLICATIONS

WO2020173112 Liu et al, Sep. 3, 2020; machine English translation.*
English machine translation of WO2020173112; PCT/CN2019/113571 filed Oct. 28, 2019.*
Zheng. Zhaojun et al. "Physicochemical and antioxidative characteristics of black bean protein hydrolysates obtained from different enzymes." Food Hydrocolloids, vol. 97, Jul. 12, 2019 (Jul. 12, 2019), pp. 1-9.
Sun. Hongxia et al.Effection of Infrared Heating on Soybean Protein Denaturation of Damp and Hot, Science and Technology of Food Industry, No. No. 05, Dec. 31, 2017 (Dec. 31, 2017), pp. 196-198.
Zhang,Junhui et al. Antioxidant activities of the rice endosperm protein hydrolysate: identification of the active peptide, Eur Food Res Technol (2009) 229:709-719, Jun. 23, 2019.

* cited by examiner

*Primary Examiner* — Sheridan Swope
(74) *Attorney, Agent, or Firm* — IPro, PLLC

(57) ABSTRACT

The disclosure provides an active peptide with an anti-lipid oxidation function and a preparation method and application thereof and belongs to the technical field of plant-derived biologically active peptides. In the disclosure, oil processing by-products, namely oil crops after oil extraction, are used as the raw materials, and the raw materials are subjected to the steps of protein extraction, infrared pretreatment, proteolysis, freeze-drying, lipophilic part extraction, vacuum concentration and drying to prepare an anti-lipid oxidation peptide having the functional characteristics of scavenging DPPH free radicals, chelating metal ions, inhibiting lipid peroxidation, prolonging vegetable oil oxidation induction time, improving emulsion stability and the like. The anti-lipid oxidation peptide can be used as a natural antioxidant in the storage and preservation of lipid and other lipid-containing food, the problems of product deterioration and harmful product production caused by lipid oxidation are solved, and the shelf life of food is prolonged.

5 Claims, 2 Drawing Sheets

PREPARATION METHOD AND APPLICATION THEREOF OF PEPTIDES WITH ANTI-LIPID-OXIDATION CAPABILITY

TECHNICAL FIELD

The disclosure belongs to the technical field of plant-derived bioactive peptides and specifically relates to the preparation method and application thereof of peptides with anti-lipid-oxidation capability.

BACKGROUND

Lipid occupies a very important position in both people's daily life and chemical industry, and with the continuous progress of edible oil production and processing technology, the application range of lipid is more and more extensive. As one of main raw materials in food industry, the quality and oxidative stability of lipid directly affect the quality of food. With the continuous improvement of people's life, the requirements for food quality are also increasing. Therefore, it is very important to deeply know and understand the oxidation process of lipid and to study and develop methods for retarding the lipid oxidation.

In recent years, antioxidant peptides have become attractive natural antioxidants due to their wide sources and high safety. Since Pokorn proposed that "some peptides and protein hydrolysates can reduce the auto-oxidation rate and lipid peroxide content", the research on antioxidant peptides has attracted widespread attention in the food industry. Compared with the synthetic antioxidants (BHA, BHT and the like) which have toxic and side effects and are restricted to be added, antioxidant peptides have many advantages such as high stability, high activity, rich nutrition, easy absorption, safety and low toxicity.

At present, the application of antioxidant peptides in the food system is mainly focused on meat products, which achieve the purposes of antioxidation and preservation by inhibiting or retarding lipid peroxidation. Because of their low oil solubility, the antioxidant peptides currently cannot be used in the lipid systems to solve the potential safety hazards and economic losses caused by oxidation of vegetable oils. How to prepare antioxidant peptides which can be used in lipid and the mechanism of antioxidant peptides in vegetable oil systems remains to be further studied.

SUMMARY

The disclosure provides a preparation method of active peptides with anti-lipid-oxidation capability, and the method comprises the following steps:

(1) protein preparation: protein is extracted from oil crops after oil extraction and then dried to obtain dry protein powder for use;

(2) infrared pretreatment: the dry protein powder obtained in step (1) is subjected to infrared pretreatment, wherein the pretreatment temperature is 50-150° C., and the time is 5-45 min;

(3) enzymatic treatment with protease: the pretreated dry protein powder obtained in step (2) is prepared into a solution and then subjected to enzymatic treatment with protease;

(4) freeze-drying: the supernatant after enzymatic hydrolysis is subjected to freeze-drying to obtain polypeptide powder;

(5) extraction of lipophilic polypeptides: the freeze-dried polypeptide powder is dissolved in the organic solvent solution at a ratio of (1:5)-(1:15) (w/v, g/mL), subjected to ultrasonic treatment at 10-100 Hz under the temperature of 30-60° C. for 20-120 min and then centrifuged at 0-5° C., and a supernatant is collected;

(6) vacuum concentration and drying: the supernatant obtained in step (5) is subjected to vacuum concentration, and the residual organic solvent is removed to obtain an active peptide with the anti-lipid-oxidation capability.

In an embodiment of the disclosure, the oil crops have been subjected to oil extraction.

In an embodiment of the disclosure, in step (1), the oil crops are preferably crops rich in hydrophobic amino acids.

In an embodiment of the disclosure, in step (1), the oil crops are one or more of soybeans, black beans or mung beans.

In an embodiment of the disclosure, a method for extracting protein in step (1) is alkali-extraction and acid-precipitation. Specifically, oil crops after oil extraction are resolved into the diluted alkali solution with a pH of 7-10 for 0.5-5 h and centrifuged to obtain a supernatant, then the pH of the supernatant is adjusted to 3-6 with the acid solution; After centrifugation, the obtained precipitate is resuspended into water, neutralized to a pH of 6-8 and dried to obtain protein powder for use.

In an embodiment of the disclosure, in step (1), the pH is preferably adjusted to be near the isoelectric point of protein with acid solution.

In an embodiment of the disclosure, in step (1), the diluted alkali solution is any one of sodium hydroxide, potassium hydroxide, sodium bicarbonate and the like.

In an embodiment of the disclosure, in step (1), the acid is hydrochloric acid, acetic acid, citric acid or lactic acid and the like.

In an embodiment of the disclosure, in step (1), centrifugation is carried out at 8000-12000 rpm for 8-15 min.

In an embodiment of the disclosure, in step (1), drying is preferably freeze-drying, the temperature is −100° C.-−50° C., the vacuum degree is 1-15 Pa, and the drying time is 1-5 d; the specific freeze-drying operation includes freezing a neutralized protein solution into a solid state at −100° C.-−50° C. and carrying out vacuum freeze-drying at the vacuum degree of 1-15 Pa and temperature of −100° C.-−50° C. for 1-5 d.

In an embodiment of the disclosure, in step (2), the pretreatment conditions preferably include temperature of 90-120° C. for 15-25 min; unlike traditional heat treatment which uses heat conduction and convection to heat samples, in an infrared heat treatment process, the electromagnetic waves hit the surface of a material, which absorbs energy to make its internal molecules vibrate mechanically and produces heat from inside to outside, thereby gaining the purpose of heating and making heat energy evenly distributed. Through the infrared pretreatment, globular protein is denatured, and peptide chain expansion is beneficial to the increase of the contact area between protein and protease. Besides, infrared pretreatment significantly improves the functional characteristics of protein and is beneficial to the release of bioactive substances.

In an embodiment of the disclosure, in step (3), the dry protein powder is prepared into a solution with a mass-to-volume concentration of 5-20% (w/v, g/mL), preferably 5-13%.

In an embodiment of the disclosure, in step (3), the enzymatic treatment is carried out under the optimum hydrolysis conditions of protease, temperature keeping and shaking are carried out for a reaction for 0.5-15 h; after enzyme deactivation and cooling, the resultant solution is adjusted to pH 6-8, and centrifuged to obtain the supernatant.

In an embodiment of the disclosure, enzyme deactivation includes a hot water bath, an infrared method and other enzyme deactivation methods, preferably deactivation by hot water bath at 70-100° C.

In an embodiment of the disclosure, in step (3), separation includes centrifugation at 5000-10000 rpm for 5-20 min.

In an embodiment of the disclosure, in step (3), the protease is capable of specifically cleaving hydrophobic amino acids, including any one or more of alcalase, trypsin, chymotrypsin, elastase, papain, bromelain or ficin.

In an embodiment of the disclosure, in step (3), the concentration of protease is 1.5-2.5 wt %.

In an embodiment of the disclosure, in step (3), the optimum hydrolysis conditions for different proteases are: the optimum conditions for alcalase include a temperature of 40-60° C., a pH of 8.0-11.0 and a reaction time of 1-7 h; the optimum conditions for bromelain include a temperature of 40-60° C., a pH of 6.0-8.0 and a reaction time of 2-8 h; the optimum conditions for ficin include a temperature of 40-60° C., a pH of 4.0-7.0 and a reaction time of 2-8 h; the optimum conditions for trypsin include a temperature of 25-45° C., a pH of 7.0-9.0 and a reaction time of 0-5 h; the optimum conditions for chymotrypsin include a temperature of 20-50° C., a pH of 7.0-10.0 and a reaction time of 0-5 h; the optimum conditions for elastase include a temperature of 15-50° C., a pH of 6.0-9.0 and a reaction time of 0-5 h; the optimum conditions for papain include a temperature of 40-60° C., a pH of 6.0-8.0 and a reaction time of 1-8 h.

In an embodiment of the disclosure, in step (3), the supernatant is temporarily stored at 0-9° C.; in addition, if the supernatant cannot be used in time, the supernatant needs to be frozen and stored at a freezing temperature of −50° C.-0° C. When used, a freezing raw material solution needs to be thawed at a low temperature to minimize the damage to protein during freezing and thawing process.

In an embodiment of the disclosure, in step (3), cooling is preferably rapid cooling.

In an embodiment of the disclosure, in step (4), specific freeze-drying operation includes freezing the supernatant into a solid state at −100° C.-0° C. and carrying out vacuum freeze-drying at a vacuum degree of 1-15 Pa and a temperature of −100° C.-−50° C. for 1-5 d to obtain the polypeptide powder.

In an embodiment of the disclosure, in step (5), the organic solvent is any one or two of n-hexane, petroleum ether, methanol, ethanol, n-butanol or dichloromethane, preferably the mixture of ethanol and n-hexane at a ratio of (1:1)-(1:7). Preferably (1:4)-(1:5).

In an embodiment of the disclosure, in step (5), centrifugation is carried out at 5000-10000 rpm for 5-20 min.

In an embodiment of the disclosure, vacuum concentration is vacuum centrifugal concentration at 20-50° C., and a concentrated polypeptide solution is dried at 20-50° C. to remove the residual organic solvent.

The disclosure also provides an active peptide with an anti-lipid-oxidation function prepared by the method above.

Finally, the disclosure also provides the application of the active peptide with anti-lipid-oxidation capability on inhibiting lipid oxidation, as well as the lipid containing the active peptide with anti-lipid-oxidation function.

The beneficial technical effects achieved by the disclosure:

(1) The natural antioxidant (antioxidant peptide) obtained in the disclosure has the functional characteristics including scavenging DPPH free radicals, chelating metal ions, inhibiting lipid peroxidation, prolonging the oxidation induction time of vegetable oil and enhancing the stability of oil-in-water emulsions, and they can replace synthetic antioxidants with potential safety hazards to be widely used in the food industry. The active peptide with anti-lipid-oxidation capability obtained by the disclosure also has the advantages of high stability, safety and activity, which is of great significance for ensuring food safety.

(2) The peptide product prepared by the disclosure can be well dissolved in the lipid system and used as a natural antioxidant for storing and preserving lipid and other lipid-containing food. Addition of a small amount of the anti-lipid-oxidation peptide of the disclosure can achieve the effect of prolonging the oxidation induction time of vegetable oil and other lipids by 8%-50%, indicating the problem-solving of product deterioration and toxin production caused by lipid oxidation, and the extended shelf life of food.

(3) There are many by-products during oil processing in China, while these by-products ae seldom little reuse. In the disclosure, by-products derived from oil processing (namely oil crops after oil extraction) are selected as the raw materials to produce a high value-added anti-lipid-oxidation peptide product, which is of great importance for technological advancement and competitiveness strengthening of grain and oil companies and has high economic and social benefits.

(4) The disclosure has mild reaction conditions, the product can be continuously produced in large quantities, and a solid foundation is laid for the development of novel anti-lipid-oxidation agents. The development and preparation of the anti-lipid-oxidation peptide provided by the disclosure has great practical and social significance for inhibiting lipid oxidation, ensuring food safety and promoting technological progress.

DETAILED DESCRIPTION

Figure 1:
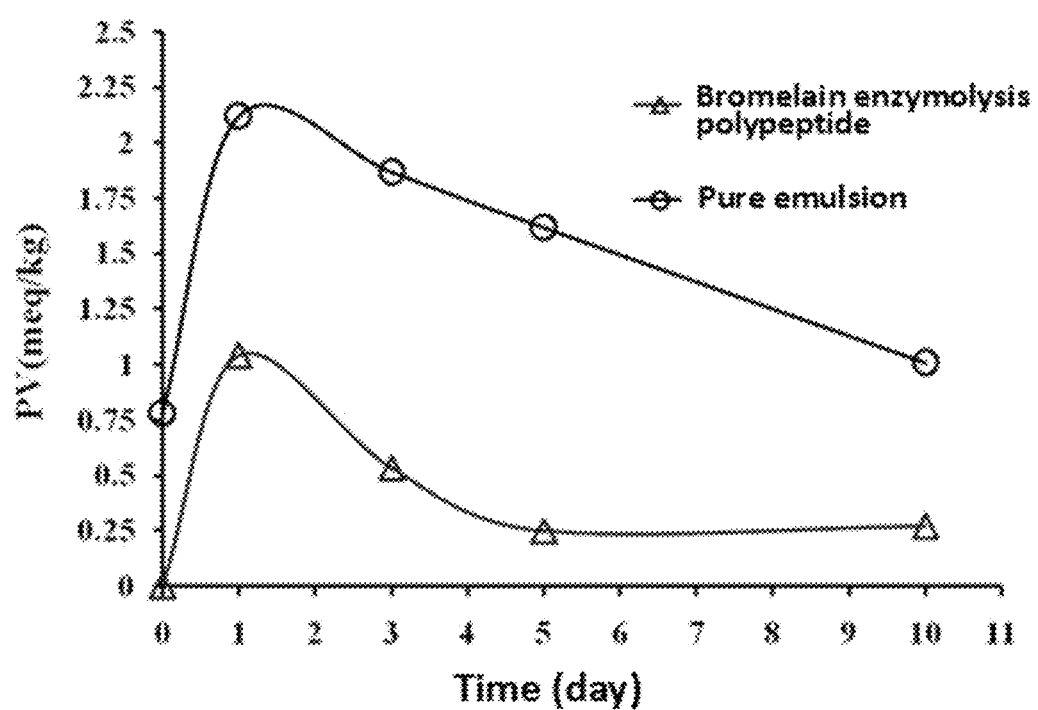
FIG. 1 shows the effects of black bean polypeptide on the peroxide value of oil-in-water emulsion.

The following examples are used to illustrate the disclosure, but not to limit the scope of the disclosure. Without departing from the spirit and essence of the disclosure, modifications or substitutions made to the methods, steps or conditions of the disclosure fall within the scope of the disclosure.

Alcalase ($2\times10^5$ U/g) is purchased from Novozymes.

Bromelain ($9\times10^4$ U/g) is purchased from J&K Scientific Co., Ltd.

Trypsin (1000-2000 units/mg), chymotrypsin ($\geq40$ units/mg), elastase ($\geq4.0$ units/mg), ficin ($2\times10^5$ U/g) and papain ($\geq10$ units/mg) are all purchased from Sigma.

Unless otherwise specified, the experimental materials, reagents and instruments and the like used in the examples of the disclosure are all commercially available. If not specifically specified, the technical means used in the examples are conventional methods well known to those skilled in the art.

In an embodiment of the disclosure, the method specifically includes:

(1) protein extraction: oil crops after oil extraction are resuspended in a dilute alkali solution with a pH of 7-10 for 0.5-5 h and centrifuged to obtain a supernatant, then the pH of the supernatant is adjusted to 3-6 with an acid, the supernatant is separated to obtain a precipitate, and the precipitate is resuspended in water, neutralized to a pH of 6-8 and dried to obtain dry protein powder;

(2) infrared pretreatment: the dry protein powder obtained in step (1) is subjected to infrared pretreatment, wherein the pretreatment temperature is 50-150° C., and the time is 5-45 min;

(3) proteolysis: the pretreated dry protein powder obtained in step (2) is prepared into a solution with a concentration of 5-20%, the pH of the solution is adjusted to the optimum pH range of protease, the solution is preheated to the optimum temperature range of protease and kept for 5-30 min, protease is added, temperature keeping and shaking are carried out for a reaction for 0.5-15 h under optimum enzymolysis conditions, enzyme deactivation and cooling are carried out, the pH of obtained pulp is adjusted to 6-8, and the pulp is centrifuged at 5000-10000 rpm for 5-20 min to obtain a supernatant so as to obtain an enzymolysis supernatant;

(4) freeze-drying: the enzymolysis supernatant is subjected to freeze-drying to obtain polypeptide powder;

(5) extraction of lipophilic polypeptides from the polypeptide powder by an ultrasonic-assisted solvent method: lipophilic components are separated by using an ultrasonic-assisted solvent method, that is to say, the freeze-dried polypeptide powder is dissolved in an organic solvent, subjected to ultrasonic treatment at 10-100 Hz at a temperature of 30-60° C. for 20-120 min and then centrifuged at 5000-10000 rpm at 0-5° C. for 5-20 min, and a supernatant is collected;

(6) vacuum concentration and drying: the supernatant obtained in step (5) is subjected to vacuum centrifugal concentration at 20-50° C. for 0.5-2 mL, and the concentrated polypeptide solution is dried at 20-50° C. to remove the residual organic solvent so as to obtain an active peptide with an anti-lipid oxidation function.

1. Measurement of DH, DPPH Free Radical Scavenging Ability and Metal Ion Chelating Ability of the Enzymolysis Supernatant Obtained in Step (3)

(1) A method for measuring DH is an o-phthalaldehyde (OPA) method, and the method is as follows:

① an OPA reagent (preparation right before use): 7.620 g of sodium tetraborate decahydrate and 200 mg of sodium dodecyl sulfate (SDS) are completely dissolved in 150 mL of deionized water first, then 160 mg of OPA (≥97%) is dissolved in 4 mL of absolute ethanol, the OPA solution is transferred into the solution above, then 176 mg of dithiothreitol (DTT) is added into the solution, and finally the solution is added to 200 mL with deionized water;

② preparation of a serine standard solution: 50 mg of serine is dissolved in 500 mL of deionized water (0.9516 meqv/L);

③ preparation of a sample solution: an enzymolysis supernatant is diluted by 5-50 times with deionized water (make the measured absorbance between 0.2-0.8) and mixed uniformly;

④ standard measurement: 400 μL of the serine standard solution is added into a test tube with a stopper containing 3 mL of the OPA reagent and shaken uniformly for an accurate reaction for 2 min at room temperature, and then the absorbance is measured at 340 nm with an ultraviolet spectrophotometer;

⑤ blank measurement: 400 μL of deionized water is added into a test tube with a stopper containing 3 mL of the OPA reagent and shaken uniformly for an accurate reaction at room temperature for 2 min, and then the absorbance is measured at 340 nm;

⑥ sample detection: 3 mL of the OPA reagent is added into 400 μL of a to-be tested sample, mixed uniformly and placed at room temperature for 2 min, and then the absorbance is measured at 340 nm;

⑦ calculation:

$$DH(\%) = \frac{\text{serine-NH}_2\text{-}\beta}{\alpha \times h_{tot}} \text{(meqv/g protein)}$$

$$\text{serine-NH}_2 = \frac{(OD_{sample} - OD_{blank})}{(OD_{standard} - OD_{blank})} \times 0.9516 \text{ meqv/L} \times X \times \frac{1}{P}$$

In the formula, serine-NH$_2$: the serine-NH$_2$ milligram equivalent contained per gram of protein;

X: dilution multiple; P: protein content of protein powder (%);

α and β of beans are constants 0.970 and 0.342 respectively, and h$_{tot}$ is constant 7.8; the typical OD standard value is 0.8; the OD blank value is 0.07.

(2) Measurement of the DPPH free radical scavenging ability, and a method is as follows:

0.1 mM DPPH is prepared with a 95% ethanol solution, 50 μL of an enzymolysis solution and 50 μL of DPPH are added into each well of a 96-well plate and shaken for 10 s for a reaction at room temperature for 30 min, and the absorbance value at a wavelength of 517 nm is measured as Asample; 50 μL of an enzymolysis solution and 50 μL of 95% ethanol are used as a control group, and the absorbance value is measured as Asample blank under the same conditions; 50 μL of DPPH and 50 μL of deionized water are used as a blank group, and the absorbance value is measured as Acontrol under the same conditions. 3 parallel samples are made for each sample, each sample is subjected to a reaction for 30 min at room temperature after shaking for 30 s, and the absorbance of each sample is measured at a wavelength of 517 nm. An equal ratio doubling dilution method is used for gradient dilution of an enzymolysis solution to measure the DPPH scavenging rate and calculate IC$_{50}$.

$$\text{scavenging rate (\%)} = \left(1 - \frac{Asample - Asample \text{ blank}}{Acontrol}\right) \times 100\%$$

(3) Measurement of the metal ion chelating ability, and a method is as follows:

50 μL of an enzymolysis solution is added into a 96-well plate, 100 μL of a 20 μM ferrous chloride solution and 100 μL of a 0.5 mM ferrozine solution are added in sequence, mixed uniformly and placed at room temperature for 10 min, and the absorbance is measured as Asample at 562 nm; 50 μL of deionized water is used to replace the enzymolysis solution as a reference, and the absorbance is measured as Asample blank under the same conditions; 50 μL of the enzymolysis solution and 200 μL of deionized water are used as a blank, the absorbance is measured as Acontrol under the same conditions, and 3 parallel samples are made for each sample. An equal ratio doubling dilution method is used for gradient dilution of an enzymolysis solution to measure the metal ion chelating ability and calculate IC$_{50}$.

$$\text{chelating rate (\%)} = \left(1 - \frac{A_{sample} - A_{sample\ blank}}{A_{control}}\right) \times 100\%$$

2. Measurement of the Ability of the Polypeptide Powder Obtained in Step (4) to Inhibit Peroxidation of Linoleic Acid and the Effect on the Oxidation Induction Time and Measurement of the Effect of the Lipid-Soluble Polypeptide Powder Obtained in Step (6) on the Oxidation Induction Time A method for linoleic acid peroxidation analysis is as follows:

① preparation of a sample solution: 1.5 mg of polypeptide is roughly dissolved in 1 mL of deionized water, 2 mL of a 50 mM phosphate buffer solution (pH 7.0), 1 mL of 2.5% linoleic acid and 1 mL of deionized water are added and mixed uniformly on a mixer, the mixer is covered, sealed and placed into a constant-temperature incubator at 60° C. for temperature keeping in the dark, and the absorbance is measured every 24 h;

② preparation of a blank reagent: 1 mL of deionized water is used to replace an enzymolysis solution;

③ positive control: a 0.1 mg/mL α-tocopherol solution is used to replace the enzymolysis solution;

④ measurement of absorbance: 5 µL of a reaction solution is taken, 235 µL of a 75% ethanol solution, 5 µL of a 30% ammonium thiocyanate solution and 5 µL of a ferrous sulfate solution (containing 3.5% HCl) are added in sequence and mixed uniformly for 3 min, the absorbance (Asample) is measured at 500 nm once a day, and the group without addition of a zymolyte is used as a blank control (Asample blank).

$$\text{inhibition rate (\%)} = \frac{A_{sample\ blank} - A_{sample}}{A_{sample\ blank}} \times 100\%.$$

A method for measurement of the oxidation induction time is as follows:

A Rancimat lipid oxidation stabilizer is used for measuring the oxidation induction time, and sunflower seed oil is as an experimental object. Parameter setting: 100-150° C., air flow rate 0.5-1.5 L/h, peptide addition amount 0.05-2%.

3. Measurement of the Anti-Lipid Oxidation Ability of Polypeptide Powder in an Oil-in-Water Emulsion System Measurement of the content of primary oxidation products (peroxide value, PV) and secondary oxidation products (TBARS method) for lipid oxidation.

A method for measuring the peroxide value (PV) is as follows:

① preparation of an emulsion: 30% (v/v, mL/mL) rapeseed oil, 1% (mL/mL) Tween 80 and 69% (mL/mL) ultrapure water are prepared into the emulsion, and the emulsion is magnetically stirred for 30 min, sheared for 2 min and homogenized;

② measurement of the PV value: the emulsion is destabilized by adding chloroform (1:2, w/v, g/mL, the same below) and sodium sulfate; after vigorously shaken for 2 min, the destabilized emulsion is centrifuged (3000 g/5 min, 4° C.), and after acetic acid (3:2, v/v mL/mL, the same below) and 0.5 mL of a potassium iodide saturated solution are added into lipid components, the following steps are repeated three times: shaking the solution vigorously for 20 s and placing the solution in the dark for 10 s. Starch (1% w/v solution) is used as an indicator, and PV is measured by a sodium thiosulfate titration method.

$$PV(meq/kg) = M*V*1000/m$$

Wherein PV: peroxide value (meq/kg); M: molar concentration (mol/L) of a sodium thiosulfate solution; V: volume (mL) of a sodium thiosulfate solution; m: sample mass (g).

A TBARS measurement method is as follows:

1.5 mL of an emulsion is taken, 1 mL of a 1% thiobarbituric acid solution and 2.5 mL of a 10% trichloroacetic acid solution (TCA) are added and mixed uniformly for a reaction in a boiling water bath for 30 min, the mixture is taken out and cooled in an ice water bath for 5 min, 2.5 mL of a sample solution is taken and added into an equal volume of trichloromethane, the mixture is centrifuged at 4500 rpm for 10 min, the supernatant is taken, and the absorbance is measured at 532 nm.

Example 1 Preparation of a Black Bean Anti-Lipid Oxidation Peptide AOP1

Black beans are rich in hydrophobic amino acids, the proportion of hydrophobic amino acids is as high as 45%, peptide fragments containing hydrophobic amino acids are more likely to react with lipid-soluble substances, and hydrophobic amino acids increase the solubility of peptides in the lipid system, so that black beans are selected as the raw materials.

(1) Protein extraction: black bean powder after oil extraction is resuspended in deionized water at 1:8 (w/v, g/mL, the same below) and stirred for 60 min, the pH is adjusted to about 8.0 with 0.015 M NaOH, the solution is stirred for 2 h and centrifuged at 8000 rpm for 15 min, the supernatant is taken, the pH is adjusted to about 4.5 with 2 M HCl, a protein precipitate obtained after centrifugation at 8000 rpm for about 15 min is resuspended in deionized water, the pH is adjusted to be neutral with 0.015 M NaOH, and finally freeze-drying is carried out to obtain black bean protein;

(2) infrared pretreatment: black bean protein powder obtained after freeze-drying is subjected to infrared heating treatment, wherein the treatment temperature is 100° C., and the time is 20 min;

(3) proteolysis: the protein powder obtained in step (2) is taken, added into deionized water at a ratio of 1:10 (w/v), shaken and mixed, the pH of the solution is adjusted to about 7.0, the solution is preheated to 55° C. and kept for 10 min, selected bromelain (concentration is 2%, w/v, g/mL, the same below) is added, the pH of the solution is adjusted to 7.0, the temperature is kept at 55° C., the solution is shaken for a reaction for 4 h, passivation and enzyme deactivation are carried out in a water bath at 95° C. for 15 min, rapid cooling is carried out, the pH of pulp is adjusted to about 7.0, and the pulp is centrifuged at 8000 rpm for 15 min and filtered to obtain an enzymolysis supernatant which is temporarily stored at 4° C.;

(4) freeze-drying: the enzymolysis solution is frozen into a solid state at −80° C., and vacuum freeze-drying is carried out at a vacuum degree of 1 Pa and a temperature of −70° C. for 3 d to obtain polypeptide powder which is dried and stored;

(5) extraction of lipophilic polypeptides: lipophilic components are separated by an ultrasonic-assisted solvent method, the freeze-dried polypeptide powder is dissolved in a mixed solution of ethanol and n-hexane at a ratio of 1:8 (w/v, g/mL) (wherein, the volume ratio of ethanol to n-hexane is 1:4), subjected to ultrasonic treatment at 80 Hz and a temperature of 45° C. for 30 min and then centrifuged at 8000 rpm and 4° C. for 15 min, and a supernatant is collected;

(6) vacuum concentration and drying: the solution above is subjected to vacuum centrifugal concentration at 45° C. to a certain volume, and the concentrated polypeptide solution is subjected to vacuum drying at 45° C. to remove the residual organic solvent so as to obtain an active peptide with an anti-lipid oxidation function.

Wherein, the DH, DPPH free radical scavenging ability and metal ion chelating ability of the enzymolysis supernatant obtained in step (3) are measured, and the measurement results are: DH is 21.74%, the $IC_{50}$ value of the DPPH free radical scavenging ability is 21.23 μg/mL, and the $IC_{50}$ value of the metal ion chelating ability is 14.12 μg/mL. From the experimental results, it can be seen that the polypeptide has a very high ability to capture peroxide free radicals and chelate metal ions and a high antioxidant capacity and is an excellent natural antioxidant.

The anti-lipid oxidation ability of the polypeptide powder (that is, the polypeptide powder without extracting the lipid-soluble polypeptide powder) obtained in step (4) in a pure oil system is measured. The ability of the polypeptide powder to inhibit peroxidation of linoleic acid and the oxidation induction time in a sunflower seed oil system are measured. 0.5% pure oil mass of the polypeptide powder is added, and the measurement results are: the linoleic acid peroxidation inhibition rate is 80%-95% in the first 5 d (with 0.1 mg/mL α-tocopherol as the control which has the inhibition rate of about 80%-95% in the first 5 d), and the oxidation induction time in the sunflower seed oil system is prolonged by 10.40% for about 26 d (with 0.5% α-tocopherol as the control which prolongs the oxidation induction time by 14.92% for about 37 d).

The effect of the active peptide with an anti-lipid oxidation function obtained in step (6) on the oxidation induction time in the sunflower seed oil system is measured. By adding only 0.5% pure oil mass of the active peptide with an anti-lipid oxidation function, the oxidation induction time can be prolonged by 49.25% for about 123 d (with 0.5% α-tocopherol as the control which prolongs the oxidation induction time by 14.92% for about 37 d).

Figure 2:
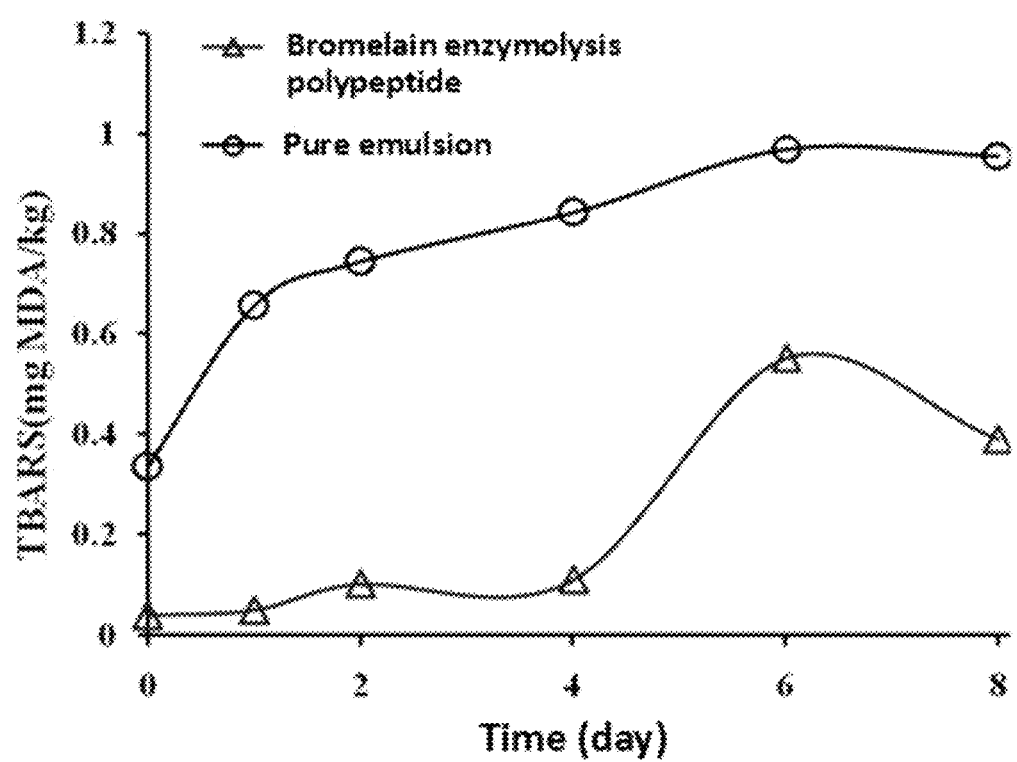
FIG. 2 shows the effects of black bean polypeptide on the TBARS value of oil-in-water emulsion.

The anti-lipid oxidation ability of the polypeptide powder obtained in step (4) in an oil-in-water emulsion system is measured, and the measurement results are shown in FIG. 1 and FIG. 2. It can be seen that in the first 7 d, the black bean peptide significantly inhibits the production amount of primary lipid oxidation products and secondary lipid oxidation products. Effective components of the polypeptide powder obtained according to indexes of the disclosure in the oil-in-water emulsion system are mainly lipid-soluble polypeptides, indirectly proving that the lipid-soluble polypeptide of the disclosure also has a good anti-lipid oxidation function.

Example 2

Mung beans are selected as the raw materials, and other steps refer to Example 1.

Comparative Example 1

When step (2) is deleted, that is to say, when infrared pretreatment is not carried out, the remaining steps and conditions are the same as those in Example 1 to prepare an active peptide with an anti-lipid oxidation function;

others remain unchanged, and a corresponding product is obtained.

The performance of the obtained product is measured, the degree of hydrolysis (DH) of an enzymolysis supernatant is 14.37%, the $IC_{50}$ value of the DPPH free radical scavenging ability is 108.05 μg/mL, and the $IC_{50}$ value of the metal ion chelating ability is 235.80 μg/mL;

the ability of the polypeptide powder obtained in Comparative Example 1 to inhibit peroxidation of linoleic acid and the effect on the oxidation induction time in a sunflower seed oil system (0.5% pure oil mass of the polypeptide powder is added) are measured, and the measurement results are: in the first 5 d, the linoleic acid peroxidation inhibition rate is maintained at about 60% (with 0.1 mg/mL α-tocopherol as the control which has the inhibition rate of about 80%-95%), and the oxidation induction time is prolonged by 2.95% for about 7 d;

the effect of the active peptide with an anti-lipid oxidation function obtained in Comparative Example 1 on the oxidation induction time in the sunflower seed oil system is measured, and by adding 0.5% pure oil mass of the active peptide with an anti-lipid oxidation function, the oxidation induction time can be prolonged by 10.23% for about 25 d (with 0.5% α-tocopherol as the control which prolongs the oxidation induction time by 14.92% for about 37 d).

Comparative Example 2

When pretreatment in step (2) is microwave (600 W, 2 min), the remaining steps and conditions are the same as those in Example 1 to prepare an active peptide with an anti-lipid oxidation function;

others remain unchanged, and a corresponding product is obtained.

The performance of the obtained product is measured, the degree of hydrolysis (DH) of an enzymolysis supernatant is 16.21%, the $IC_{50}$ value of the DPPH free radical scavenging ability is 83.41 μg/mL, and the $IC_{50}$ value of the metal ion chelating ability is 135.48 μg/mL;

the ability of the polypeptide powder obtained in step (4) in Comparative Example 2 to inhibit peroxidation of linoleic acid and the effect on the oxidation induction time in a sunflower seed oil system (0.5% pure oil mass of the polypeptide powder is added) are measured, and the measurement results are: in the first 5 d, the linoleic acid peroxidation inhibition rate is maintained at about 80% (with 0.1 mg/mL α-tocopherol as the control which has the inhibition rate of about 80%-95%), and the oxidation induction time is prolonged by 4.65% for about 11 d;

the effect of the active peptide with an anti-lipid oxidation function obtained in step (6) in Comparative Example 2 on the oxidation induction time in the sunflower seed oil system is measured, and by adding 0.5% pure oil mass of the active peptide with an anti-lipid oxidation function, the oxidation induction time can be prolonged by 28.46% for about 71 d (with 0.5% α-tocopherol as the control which prolongs the oxidation induction time by 14.92% for about 37 d).

Comparative Example 3

Infrared pretreatment in step (2) is changed to oven heating at a treatment temperature of 100° C. for 20 min, and the remaining steps and conditions are the same as those in Example 1 to prepare an active peptide with an anti-lipid oxidation function;

others remain unchanged, and a corresponding product is obtained.

The performance of the obtained product is measured, the degree of hydrolysis (DH) of an enzymolysis supernatant is 14.05%, the $IC_{50}$ value of the DPPH free radical scavenging ability is 85.44 µg/mL, and the $IC_{50}$ value of the metal ion chelating ability is 205.41 µg/m L;

the ability of the polypeptide powder obtained in step (4) in Comparative Example 3 to inhibit peroxidation of linoleic acid and the effect on the oxidation induction time in a sunflower seed oil system (0.5% pure oil mass of the polypeptide powder is added) are measured, and the measurement results are: in the first 5 d, the linoleic acid peroxidation inhibition rate is maintained at 60%-75% (with 0.1 mg/mL α-tocopherol as the control which has the inhibition rate of about 80%-95%), and the oxidation induction time is prolonged by 3.43% for about 9 d;

the effect of the active peptide with an anti-lipid oxidation function obtained in step (6) in Comparative Example 3 on the oxidation induction time in the sunflower seed oil system is measured, and by adding 0.5% pure oil mass of the active peptide with an anti-lipid oxidation function, the oxidation induction time can be prolonged by 15.67% for about 39 d (with 0.5% α-tocopherol as the control which prolongs the oxidation induction time by 14.92% for about 37 d).

Comparative Example 4

A lipophilic component extraction method in step (5) is changed, and the remaining steps and conditions are the same as those in Example 1: freeze-dried polypeptide powder is dissolved in an 80% ethanol solution, heated for dissolution, treated at 45° C. for 30 min and then centrifuged at 8000 rpm and 4° C. for 15 min, and a supernatant is collected; the supernatant is subjected to vacuum concentration and drying to obtain lipid-soluble polypeptide powder;

others remain unchanged, and a corresponding product is obtained.

The effect of the active peptide with an anti-lipid oxidation function obtained in step (6) in Comparative Example 4 on the oxidation induction time in a sunflower seed oil system is measured, and it is found that the powder cannot be stably dispersed in the sunflower seed oil system and has low anti-lipid oxidation ability. By adding 0.5% pure oil mass of the active peptide with an anti-lipid oxidation function, the oxidation induction time can be prolonged by 18.55% for about 46 d (with 0.5% α-tocopherol as the control which prolongs the oxidation induction time by 14.92% for about 37 d).

Comparative Example 5

A lipophilic component extraction method in step (5) is changed, and the remaining steps and conditions are the same as those in Example 1: freeze-dried polypeptide powder is dissolved in an equal amount of n-hexane, heated for dissolution, treated at 45° C. for 30 min and then centrifuged at 8000 rpm and 4° C. for 15 min, and a supernatant is collected; the supernatant is subjected to vacuum concentration and drying to obtain corresponding lipid-soluble polypeptide powder;

others remain unchanged, and a corresponding product is obtained.

The effect of the active peptide with an anti-lipid oxidation function obtained in step (6) in Comparative Example 5 on the oxidation induction time in a sunflower seed oil system is measured, and it is found that the powder has a low yield, can be dissolved and dispersed in the sunflower seed oil system and has low anti-lipid oxidation ability. By adding 0.5% pure oil mass of the active peptide with an anti-lipid oxidation function, the oxidation induction time can be prolonged by 14.01% for about 35 d (with 0.5% α-tocopherol as the control which prolongs the oxidation induction time by 14.92% for about 37 d).

Comparative Example 6

A lipophilic component extraction method in step (5) is changed, and the remaining steps and conditions are the same as those in Example 1: freeze-dried polypeptide powder is dissolved in absolute ethanol (1:10, w/v, g/mL), heated for dissolution, treated at 45° C. for 30 min and then centrifuged at 8000 rpm and 4° C. for 15 min, and a supernatant is collected; the supernatant is subjected to vacuum concentration and drying to obtain corresponding lipid-soluble polypeptide powder;

others remain unchanged, and a corresponding product is obtained.

The effect of the active peptide with an anti-lipid oxidation function obtained in step (6) in Comparative Example 5 on the oxidation induction time in a sunflower seed oil system is measured, and it is found that the powder is partially dispersed in the sunflower seed oil system and has low anti-lipid oxidation ability. By adding 0.5% pure oil mass of the active peptide with an anti-lipid oxidation function, the oxidation induction time can be prolonged by 10.23% for about 26 d (with 0.5% α-tocopherol as the control which prolongs the oxidation induction time by 14.92% for about 37 d).

Example 3 Optimization of Extraction Systems in the Process of Extracting Lipophilic Polypeptides The volume ratio of a mixed solution in step (5) is 1:1, 1:2, 1:3, 1:4 or 1:5, and the remaining steps and conditions are the same as those in Example 1 to prepare an active peptide with an anti-lipid oxidation function;

others remain unchanged, and a corresponding product is obtained.

The effect of the active peptide with an anti-lipid oxidation function on the oxidation induction time in a sunflower seed oil system is measured, and results are shown in Table 1.

TABLE 1

Performance results of active peptides obtained from different lipophilic polypeptide extraction systems

| Ethanol:n-hexane | Dispersion effect | Anti-oxidation effect |
| --- | --- | --- |
| 1:1 | Poor dispersibility, partly insoluble | Shorten the oxidation induction time by 9.19% |
| 1:2 | Poor dispersibility, insoluble in a small amount | Prolong the oxidation induction time by 21.20% |
| 1:3 | Acceptable but unstable dispersibility | Prolong the oxidation induction time by 27.31% |
| 1:4 | Good dispersibility and solubility | Prolong the oxidation induction time by 49.25% |
| 1:5 | Good dispersibility and solubility | Prolong the oxidation induction time by 34.08% |

Although the disclosure has been disclosed as above in preferred examples, it is not intended to limit the disclosure. Anyone familiar with this technology can make various changes and modifications without departing from the spirit and scope of the disclosure. Therefore, the protection scope of the disclosure should be defined by the claims.

What is claimed is:

1. A method for preparing an active peptide with an anti-lipid oxidation function, comprising the following steps:
   extracting protein from oil crops after oil extraction and then drying to obtain dry protein powder, wherein the oil crop is black beans;
   treating the dry protein powder with infrared, wherein the treating is at a temperature of 0° C. to 150° C. for 5 minutes to 45 minutes;
   preparing a solution by adding the treated dry protein powder to liquid and adding the protease bromelain to obtain an enzymolysis product;
   freeze-drying a centrifugation supernatant of the enzymolysis product to obtain polypeptide powder;
   dissolving the freeze-dried polypeptide powder in an organic solvent, and subjecting the dissolved polypeptide powder to ultrasonic treatment at 10 Hz to 100 Hz at 30° C. to 60° C. for 20 minutes to 120 minutes, and then centrifuging at 0° C. to 5° C. and collecting the supernatant;
   and
   concentrating the supernatant by vacuum and removing residual organic solvent to obtain the active peptide with the anti-lipid oxidation function.

2. The preparation method according to claim 1, wherein extracting the protein comprises:
   suspending the oil crops in a dilute alkali solution with a pH of 7 to 10 for 0.5 hours to 5 hours and centrifuging to obtain a supernatant,
   adjusting a pH of the supernatant to 3 to 6 with an acid,
   separating the supernatant to obtain a precipitate,
   resuspending the precipitate in water,
   neutralizing to a pH of 6 to 8, and
   drying.

3. The preparation method according to claim 1, wherein concentrating the protease by vacuum yields a concentration of 1.5 wt % to 2.5 wt %; and wherein the dry protein powder has a mass-to-volume concentration of 5% to 20% (g/mL).

4. The preparation method according to claim 2, wherein concentrating the protease by vacuum yields a concentration of 1.5 wt % to 2.5 wt %; and wherein the dry protein powder has a mass-to-volume concentration of 5% to 20% (g/mL).

5. The preparation according to claim 1, wherein the organic solvent is any one or more of n-hexane, petroleum ether, methanol, ethanol, n-butanol, or dichloromethane.

* * * * *